US010729745B2

United States Patent
Arnoult et al.

(10) Patent No.: US 10,729,745 B2
(45) Date of Patent: Aug. 4, 2020

(54) USE OF LA1-LIKE PEPTIDE ISOLATED FROM MAURUS PALMATUS VENOM AS AN ACTIVATOR OF SPERM MOTILITY IN MAMMALS

(71) Applicant: IMV Technologies, Saint Ouen sur Iton (FR)

(72) Inventors: Christophe Arnoult, Saint Etienne de Crossey (FR); Eric Schmitt, Villaines-la-Juhel (FR); Guillaume Martinez, Grenoble (FR); Pierre Ray, Biviers (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 0 days.

(21) Appl. No.: 16/306,289

(22) PCT Filed: Jun. 1, 2017

(86) PCT No.: PCT/EP2017/063340
§ 371 (c)(1),
(2) Date: Nov. 30, 2018

(87) PCT Pub. No.: WO2017/207705
PCT Pub. Date: Dec. 7, 2017

(65) Prior Publication Data
US 2019/0151412 A1 May 23, 2019

(30) Foreign Application Priority Data
Jun. 2, 2016 (EP) .................................... 16305642

(51) Int. Cl.
*A61K 35/646* (2015.01)
*A61K 38/17* (2006.01)
*C07K 14/435* (2006.01)
*A61P 15/08* (2006.01)
*G01N 33/50* (2006.01)

(52) U.S. Cl.
CPC ........ *A61K 38/1767* (2013.01); *A61K 35/646* (2013.01); *A61P 15/08* (2018.01); *C07K 14/43522* (2013.01); *G01N 33/5029* (2013.01); *G01N 2333/43521* (2013.01)

(58) Field of Classification Search
None
See application file for complete search history.

(56) References Cited

FOREIGN PATENT DOCUMENTS

CN 101590122 A 12/2009

OTHER PUBLICATIONS

Luna-Ramirez et al. (Toxicon 63 (2013) 44-54) (Year: 2013).*
NCBI sequence API81331.1 (downloaded online on Aug. 21, 2019 from URL:< https://blast.ncbi.nlm.nih.gov/Blast.cgi>) (Year: 2019).*
Abdel-Rahman et al., "Venom proteomic and venomous glands transcriptomic analysis of the Egyptian scorpion*Scorpio maurus palmatus*(Arachnida: Scorpionidae)" Toxicon Elmsford, vol. 74, pp. 193-207 (Aug. 2018).
Harrison et al., "Characterisation of three alpha-helical antimicrobial peptides from the venom of*Scorpio maurus palmatus*", Toxicon, vol. 117, pp. 30-36 (Mar. 2016).
El-Bitar et al., "Virocidal activity of Egyptian scorpion venoms against hepatitis C virus", Virology Journal, vol. 12, No. 1, pp. 1-9, (2015).
Luna-Ramirez et al., "Characterization of the venom from the Australian scorpion*Urodacus yaschenkoi*: Molecular mass analysis of components, cDNA sequences and peptides with antimicrobial activity", Toxicon, vol. 63, pp. 44-54 (Nov. 2012).
Terriou et al., "Papaverine as a replacement for pentoxifylline to select thawed testicular or epididymal spermatozoa before ICSI", Gynecologie Obstetrique & Fertilite, pp. 786-790, (Nov. 2015).
An J et al., "Use of traditional Chinese medicine composition comprising ginseng, leech, woodlouse, frankincense (prepared), and red paeonia, in preparing medicine for treating male infertility", Database WPI, pp. 1-2 XP002763998—English Language Abstract of Chinese Patent 101590122A (Dec. 2009).
Yibao et al., "Extreme diversity of scorpion venom peptides and proteins revealed by transcriptomic analysis: Implication for proteome evolution of scorpion venom arsenal", Journal of Proteomics, pp. 1563-1576 (Dec. 2011).

* cited by examiner

Primary Examiner — Sergio Coffa
(74) Attorney, Agent, or Firm — Browdy and Neimark, PLLC

(57) ABSTRACT

The invention relates to a La-1-like peptide agent that increases sperm motility. It is non-toxic and it may be used to treat male infertility in humans, and also to increase fertility in animals. It may be used in artificial reproductive techniques such as in vitro fertilisation (IVF), including intra-cytoplasmic sperm injection (ICSI). The La-1 like peptide agent may also be used in artificial insemination techniques such as intra-cytoplasmic uterine injection (IUI).

16 Claims, 6 Drawing Sheets

Specification includes a Sequence Listing.

SEQUENCE LISTING

<160> NUMBER OF SEQ ID NOS: 8

<210> SEQ ID NO 1
<211> LENGTH: 73
<212> TYPE: PRT
<213> ORGANISM: S Maurus palmatus

<400> SEQUENCE: 1

Ser Gly Glu Ser Cys Lys Ala Gly Lys Phe Thr Val Leu Val Gly His
1               5                   10                  15

Gln Gln Asn Asp Lys Ser Thr Cys Thr Leu Tyr Lys Cys Leu Asn Phe
            20                  25                  30

Lys Arg Lys Tyr Ala Leu Gln Ile Ser Ser Cys Ala Asp Val Asp Leu
        35                  40                  45

Lys Ser Gly Cys Arg Gln Val Pro Gly Ala Ala Ser Ala Asn Phe Pro
    50                  55                  60

Glu Cys Cys Pro Met Val Ile Cys Lys
65                  70

<210> SEQ ID NO 2
<211> LENGTH: 24
<212> TYPE: PRT
<213> ORGANISM: S Maurus palmatus

<400> SEQUENCE: 2

Met Glu His Ala Leu Lys Ser Leu Leu Leu Ile Cys Leu Val Val Phe
1               5                   10                  15

Ser Phe Thr Ser Leu Cys Met Gly
            20

<210> SEQ ID NO 3
<211> LENGTH: 98
<212> TYPE: PRT
<213> ORGANISM: S Maurus palmatus

<400> SEQUENCE: 3

Met Glu His Ala Leu Lys Ser Leu Leu Leu Ile Cys Leu Val Val Phe
1               5                   10                  15

Ser Phe Thr Ser Leu Cys Met Gly Ser Gly Glu Ser Cys Lys Ala Gly
            20                  25                  30

Lys Phe Thr Val Leu Val Gly His Gln Gln Asn Asp Lys Ser Thr Cys
        35                  40                  45

Thr Leu Tyr Lys Cys Leu Asn Phe Lys Arg Lys Tyr Ala Leu Gln Ile
    50                  55                  60

Ser Ser Cys Ala Asp Val Asp Leu Lys Ser Gly Cys Arg Gln Val Pro
65                  70                  75                  80

Gly Ala Ala Ser Ala Asn Phe Pro Glu Cys Cys Pro Met Val Ile Cys
                85                  90                  95

Lys Gly

<210> SEQ ID NO 4
<211> LENGTH: 97
<212> TYPE: PRT
<213> ORGANISM: S Urodacus yaschenkoi

<400> SEQUENCE: 4

Met Glu Arg Ile Leu Lys Pro Val Phe Leu Ala Ile Leu Ile Val Leu
1               5                   10                  15

Ser Phe Ser Ser Gln Cys Met Gly Phe Gly Glu Ser Cys Gln Ala Gly

```
                    20                  25                  30

Lys His Ile Val Pro Val Gly Gln Gln Gln Ile Asp Ser Ser Thr Cys
            35                  40                  45

Thr Leu Tyr Lys Cys Ser Asn Tyr Asn Arg Lys Tyr Ala Leu Glu Thr
 50                  55                  60

Thr Ser Cys Ala Thr Leu Lys Met Lys Ser Gly Cys Arg Met Val Pro
 65                  70                  75                  80

Gly Ala Ala Thr Ala Pro Phe Pro Asn Cys Cys Pro Met Met Met Cys
            85                  90                  95

Lys

<210> SEQ ID NO 5
<211> LENGTH: 73
<212> TYPE: PRT
<213> ORGANISM: H Liocheles australasiae

<400> SEQUENCE: 5

Phe Gly Glu Ser Cys Ile Ala Gly Arg Phe Ile Val Pro Leu Gly Gln
 1               5                  10                  15

Gln Val Thr Asp Gln Arg Asp Cys Ala Leu Tyr Lys Cys Val Asn Tyr
            20                  25                  30

Asn Lys Lys Phe Ala Leu Glu Thr Lys Arg Cys Ala Thr Val Asn Leu
         35                  40                  45

Lys Ser Gly Cys Lys Thr Val Pro Gly Gly Ala Gly Ala Ala Phe Pro
     50                  55                  60

Ser Cys Cys Pro Met Val Thr Cys Lys
 65                  70

<210> SEQ ID NO 6
<211> LENGTH: 101
<212> TYPE: PRT
<213> ORGANISM: S Pandinus cavimanus

<400> SEQUENCE: 6

Met Ser His Leu Arg Ile Ala Val Ile Phe Leu Cys Thr Leu Phe Ala
 1               5                  10                  15

Leu Thr Ala Gly Ala Glu Glu Ser Cys Gln Val Gly Gly Leu Thr Ile
            20                  25                  30

Pro Val Gly Lys Thr Gln Gln Asp Arg Cys Thr Leu Tyr Glu Cys Thr
         35                  40                  45

Met Glu Ser Asn Arg Val Val Leu Lys Ser Met Ile Cys Ala Glu Gln
     50                  55                  60

Ser Leu Arg Arg Gly Cys Lys Arg Val Pro Ala Gln Ala Thr Ala Pro
 65                  70                  75                  80

Phe Pro Asp Cys Cys Pro Thr Thr Leu Cys Arg Gly Arg Gln Trp Asp
            85                  90                  95

Arg Pro Arg Thr Leu
            100

<210> SEQ ID NO 7
<211> LENGTH: 99
<212> TYPE: PRT
<213> ORGANISM: H Opisthacanthus cayaporum

<400> SEQUENCE: 7

Met Lys Ile Ala Cys Thr Leu Val Leu Phe Val Met Leu Arg Cys Tyr
 1               5                  10                  15
```

-continued

```
Val Asn Ala Arg Asn Ile Pro Gly Thr Cys Arg Thr His Thr Gly Ile
            20                  25                  30

Ile Leu Leu Ser Gly Glu Glu Trp Lys Asp Pro Asn His Cys Ser Thr
            35                  40                  45

Tyr Arg Cys Ser Arg Ile Phe Asp Gly Glu Ala Glu Leu Glu Gly Val
        50                  55                  60

Thr Cys Ala Ala Tyr His Val Pro Pro His Cys Arg Leu Val Ser Ala
65                  70                  75                  80

Ala Asn Glu Leu Tyr Pro Gln Cys Cys Pro Thr Val Ile Cys Ser Asp
                85                  90                  95

Lys Ser Arg

<210> SEQ ID NO 8
<211> LENGTH: 123
<212> TYPE: PRT
<213> ORGANISM: B Mesobuthus martensii

<400> SEQUENCE: 8

Met Ser Ile Lys Ile Ser Ala Ile Ala Leu Phe Met Leu Ser Phe Thr
1               5                   10                  15

Val Phe Val Asn Gly Ile Pro Phe Phe Leu Thr Lys Gly Arg Ile Asp
            20                  25                  30

Thr Cys Lys Thr Leu Thr Gly Glu Thr Ile Lys Ile Gly Glu Ser Trp
            35                  40                  45

His Asp Pro Asn Ser Cys Ser Val Tyr Tyr Cys Glu Val Asn Ser Leu
        50                  55                  60

Gly Ala Met Leu Ile Gly Lys Thr Cys Ala Thr Val Phe Tyr Pro Ser
65                  70                  75                  80

Asn Cys Arg Glu Glu Pro Gly Thr Gly Leu Tyr Pro Asp Cys Cys Asn
                85                  90                  95

Lys Val Val Cys Gly Glu Glu Glu Met Val Val Tyr Pro Tyr Glu Glu
                100                 105                 110

Arg Ser Leu Arg Arg Tyr Tyr Phe Ser Lys Phe
            115                 120
```

USE OF LA1-LIKE PEPTIDE ISOLATED FROM MAURUS PALMATUS VENOM AS AN ACTIVATOR OF SPERM MOTILITY IN MAMMALS

FIELD OF THE INVENTION

This invention relates to the treatment of male infertility by improving sperm motility in either in vitro or in vivo assisted reproduction techniques. The invention also relates to increasing the fertility of male animals in animal production methods, including artificial insemination.

BACKGROUND TO THE INVENTION

Infertility affects one in six couples, with, in one out of two cases, a deficiency of the male partner.

Male infertility presents highly variable phenotypes. One of the most common is asthenozoospermia, characterized by the decrease or absence of sperm motility [see Publicover S J, Barratt C L. *Sperm motility: things are moving in the lab!* Mol Hum Reprod. 2011 August; 17(8):453-6.]

Assisted reproduction technology (ART) is the term used to describe the methods used to aid couples and includes, depending on the severity of the male infertility: intrauterine insemination (IUI) for mild, in vitro fertilization (IVF) for moderate, and intra-cytoplasmic sperm injection (ICSI) for men with severe sperm dysfunction.

In some cases of azoospermia or oligozoospermia, the recovery of sperm directly from the testicle or epididymis is required.

Freezing of sperm samples is often necessary in ART. However, a major disadvantage of freezing samples is that spermatazoa that have been previously frozen, once thawed, have a reduced motility compared to fresh sperm samples, with lower amount of progressive sperm.

Moreover, in farm animals, for which artificial insemination AI is heavily used, the decreased motility of frozen sperm means that sperm concentration in straws must be increased and this reduces the overall success of the method.

The use of non-toxic agents that can increase sperm motility thus presents a strong therapeutic value in the context of medically assisted reproduction.

As spermatazoa mature in a heterogeneous manner, individual testicular spermatazoa that have been collected from a patient presenting with azoospermia or oligozoospermia are often chosen for use in medically assisted reproduction, based on their response to molecules that activate sperm motility. Very few or none, depending of the country, of these molecules are available for clinical use today, thus leaving clinicians without tools to make this selection.

As well as for in vitro fertilisation (IVF) techniques, these agents are also of interest for artificial insemination (AI), for example, where sperm is injected into the vaginal tract or uterus (IUI) of the female, because they increase the motility of the spermatozoa in the female genital tract, and therefore increase the chance of fertilization occurring.

Thus, such agents also impact the success rate of in vitro fertilization techniques, not only for therapeutic use in humans, but also for industrial reproduction use in numerous species, like horses, pigs, cattle, and birds, like for example, turkeys.

In the past, non-selective phosphodiesterase inhibitors like pentoxifylline (PTF) were used to increase the sperm motility in humans. However, while these molecules do show increased acceleration in mobile spermatazoa, a significant disadvantage has been premature stimulation of the acrosome reaction (AR). This leads to the sperm's inability to penetrate the oocyte once it reaches it.

Recently other PDE inhibitors have been examined in a small clinical trial [Tardif S, Madamidola O A, Brown S G, Frame L, Lefièvre L, Wyatt P G, Barratt C L, Martins Da Silva S J. *Clinically relevant enhancement of human sperm motility using compounds with reported phosphodiesterase inhibitor activity*. Hum Reprod. 2014, Oct. 10; 29(10)2123-35.] Of 43 commercially available molecules with PDE inhibitory activity, six showed a strong effect on poor motility in Phase I, and in Phase II three of these compounds were identified as "promising candidates for further study".

Another PDE inhibitor, papaverine, has also been considered as an alternative to pentoxifylline (see for example Terriou et al. 2015, Gynécologie Obstétrique et Fertilité 43, p. 786-790).

Therefore, there still exists a strong need for non-toxic agents that increase the motility of sperm cells to be used in ART procedures including, for example, AI, IUI, IVF, including intra-cytoplasmic sperm injection (ICSI) for therapeutic use in humans. There is a need for non-toxic agents that activate the motility of spermatazoa.

There is a need for agents that allow the selection of individual spermatozoa for use in ART including IVF, including intra-cytoplasmic sperm injection (ICSI).

There is also a strong need for agents that may be used to increase male fertility in industrial artificial insemination procedures in animals. In particular, there is a need for molecules that can increase the number of progressive sperm from a frozen straw (sample).

There is a need for an agent that can increase the fertilisation capability of a sperm population contained in a sample for use in industrial artificial insemination procedures in animals.

There is a need for an agent that is capable of activating/increasing the motility of fresh spermatozoa as well as of those that have been previously frozen.

There is a need for an agent that can activate the motility of testicular, epididymal and/or ejaculated sperm in bovine, porcine, ovine, birds, such as for example chicken and turkeys, equine, goat, and domestic animals, in particular cats and dogs.

There is a need for agents that can activate the motility of testicular, epididymal and/or ejaculated sperm in humans.

SUMMARY OF THE INVENTION

The inventors have discovered a La-1-like peptide compound that may be used to increase the motility of mammalian sperm. The applicants have demonstrated that a peptide isolated from the venom of the scorpion *Maurus palmatus*, previously identified as La1-like protein [Abdel-Rahman, M. A, et al Toxicon 74 (2013) *Venom proteomic and venomous glands transcriptomic analysis of the Egyptian scorpion Scorpio Maurus palmatus* (Arachnida: Scorpionidae) pp. 193-207] but with unknown biological function, presents an important biological activity. The peptide sequence is SEQ ID NO. 1.

The invention concerns a La-1-like peptide agent comprising SEQ ID NO. 1 or a peptide having at least 60%, 70%, 80%, 90% or 95% amino acid sequence identity with SEQ ID NO.1, for use as a medicament.

According to an embodiment of the invention, said La-1-like peptide agent may be used for the treatment of male infertility in mammals. In particular, male infertility that is partially or totally due to poor sperm mobility, may be treated using the La-1-like peptide agent of the invention.

According to an embodiment of the invention, said La-1-like peptide agent may be used to activate the motility of mammalian sperm. Contact of the agent with mammalian sperm may increase its velocity. Furthermore, non-motile sperm may become motile.

According to an embodiment of the invention, said sperm is chosen from sperm from humans, bovine, porcine, ovine, equine, goat, and domestic animals, in particular cats and dogs.

According to an embodiment of the invention, said sperm may have been previously frozen, or has been freshly ejaculated, or recovered from the epididymis, or from the testicle.

According to an embodiment of the invention, the La-1-like peptide agent may be brought into contact in vitro, with the sperm to be used in an artificial insemination procedure or in an in vitro fertilization procedure, in particular, intra-cytoplasmic sperm injection (ICSI).

According to an embodiment of the invention, the La-1-like peptide agent may be brought into contact in vivo, with sperm to be used in a natural or artificial insemination procedure.

According to an embodiment of the invention, the La-1-like peptide agent may be in the form of a pharmaceutical composition for administration to the vaginal tract and/or cervix of a female before insemination (either artificial or natural insemination).

According to an embodiment of the invention, the La-1-like peptide agent may be used in the selection of suitable sperm for a human in vitro fertilization procedure, in particular, intra-cytoplasmic sperm injection (ICSI).

According to an embodiment of the invention, the sperm to be treated may have an initial motility of between 1 and 30 µm/s.

According to an embodiment of the invention, the sperm to be treated may have an initial motility of at least 30 µm/s.

The invention also concerns a method of selection of sperm for use in a human in vitro fertilization procedure comprising the steps:
 a. bringing into contact a sperm sample with a therapeutically effective amount of La-1-like peptide agent comprising SEQ ID NO. 1 or a peptide having at least 60%, 70%, 80%, 90% or 95% amino acid sequence identity with SEQ ID NO.1;
 b. observing and measuring sperm mobility using at least one parameter chosen from track speed, path velocity, natural amplitude, non-progressive velocity and progressive velocity;
 c. selecting the most motile sperm according to the criteria used in the particular IVF procedure to be used.

The invention also concerns a method for increasing the fertility of an animal, comprising:
 a. incubating a sperm sample from an animal with a therapeutically effective amount of La-1-like peptide agent comprising SEQ ID NO. 1 or a peptide having at least 60%, 70%, 80%, 90% or 95% amino acid sequence identity with SEQ ID NO.1;
 b. artificially inseminating the female animal with said sperm sample and La-1-like peptide agent;
 c. measuring the fertility rate.

The superiority of the La-1-like peptide compared to papaverine has been observed in tests by the applicants. The applicants have also showed that the peptide presents no toxicity on sperm, and has a long lasting effect on sperm motility.

DETAILED DESCRIPTION

Figure 1A:
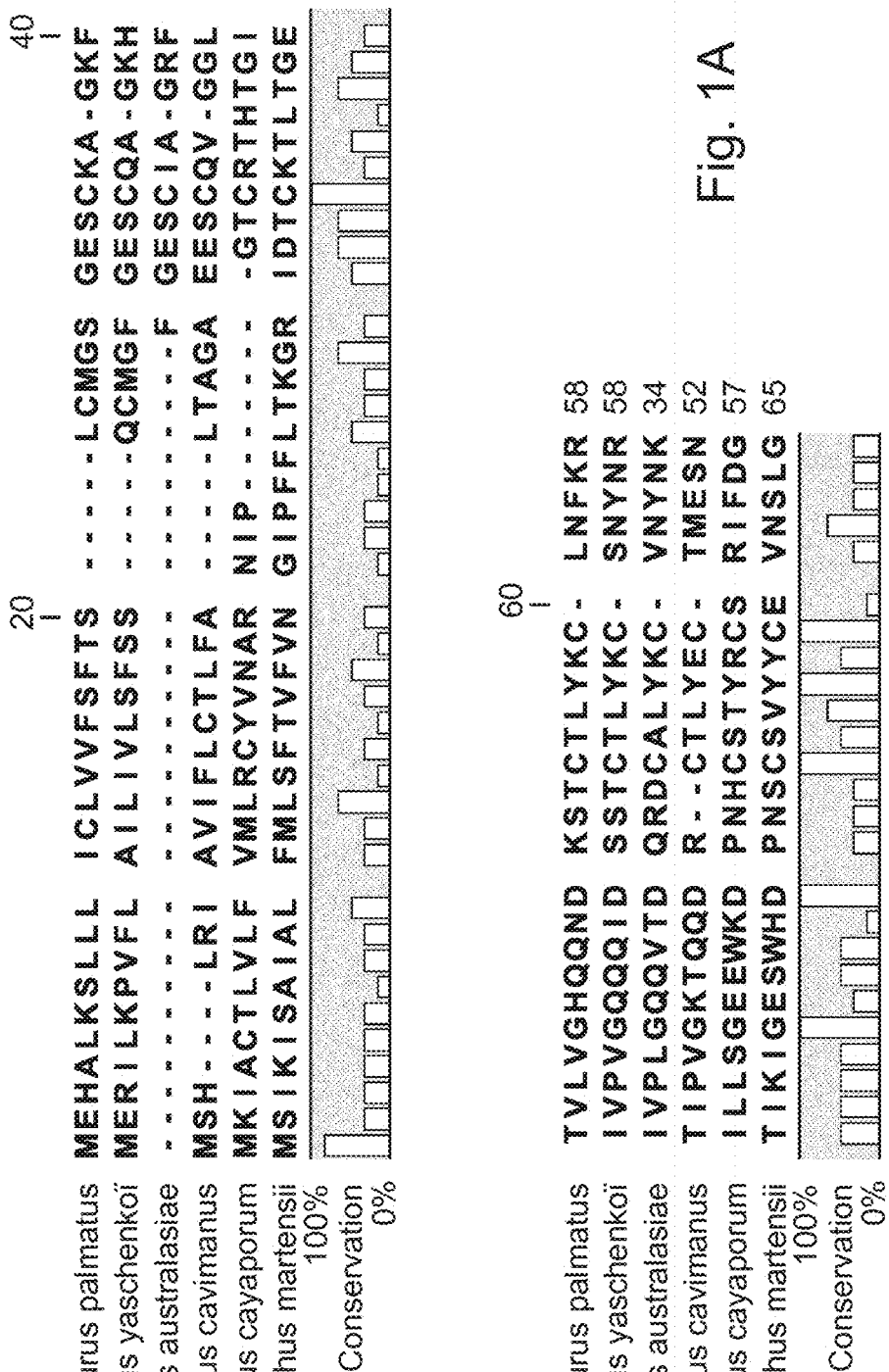
FIGS. 1A and 1B: Sequence alignment of La-1-like peptide from different species of scorpion using software CLC sequence viewer.

In the present invention, the term "motility activation" or "sperm motility activation" is to be understood as meaning increasing the velocity of sperm. This means increasing the non-progressive velocity and, optionally, the progressive motility of the sperm. The term also includes increasing the velocity of non-motile sperm (i.e., those having an initial velocity of 0 µm/s).

In the present invention, the term "sperm motility activating agent" is to be understood as an agent that increases the velocity of sperm. This includes increasing the non-progressive velocity and, optionally, the progressive velocity. The agent also may increase the velocity of non-motile sperm (i.e., those having an initial velocity of 0 μm/s).

In the present invention, the term "progressive velocity" is to be understood as meaning a velocity of at least 30 μm/s.

In the present invention, the term "non-progressive velocity" is to be understood as meaning a velocity of between 1 and 30 μm/s.

In the present invention, the term "asthenozoospermia" is to be understood as meaning reduced sperm motility. Complete asthenozoospermia means that 100% immotile spermatozoa.

In the present invention, the term "progressive sperm" is to be understood as meaning sperm that have a velocity of at least 30 μm/s. In the present invention, the term "biologically active" is to be understood as meaning having a sperm motility activating activity.

In the present invention, the term "therapeutically effective amount" refers to the amount sufficient to induce a desired biological result. That result can be alleviation of the signs, symptoms, or causes of a disease, for any other desired alteration of a biological system. In particular, the result can be sperm motility activation.

In the present invention, the term "homologous" means having at least 60%, 70%, 80%, 90% or 95% amino acid sequence identity.

In the present text, "*Scorpio Maurus palmatus*" and "*Maurus palmatus*" are synonymous.

The La-1-Like Peptide Agent

The present invention concerns a La-1-like peptide agent presenting a biological activity. Specifically, the La-1-like peptide agent concerned by the present invention may activate mammalian sperm. The agent may thus be used as a therapeutic agent for treating male infertility in particular, for treating "asthenozoospermia" or "oligozoospermia". It may also be used for increasing the fertility of animals for animal production purposes.

The present invention also provides compositions comprising a therapeutically effective amount of La-1-like peptide agent that is useful for treating male infertility.

The peptide identified by the inventors has been isolated from the venom of the scorpion *Maurus palmatus*, and has 73 amino acids (SEQ ID NO. 1) and a molecular weight of approximately 7850 kDa. The applicant has identified that the peptide also exists as a propeptide (SEQ ID NO. 3) having a cleavage site between amino acid 24 and amino acid 25. Thus the N-terminal peptide of 24 amino acids MEHALKSLLLICLVVFSFTSLCMG (SEQ ID NO. 2) is cleaved off to give the peptide SEQ ID NO. 1.

The propeptide SEQ ID NO. 3 is expected to have a similar level of biological activity as SEQ ID NO. 1.

The applicants have discovered that the peptide contains four disulfide bridges. The first Cys is located at position 29/98 of SEQ ID NO. 3 and the last at 96/98. Therefore, certain N-terminal truncations of SEQ ID NO. 3, preferably that do not disrupt said di-sulfide bridges, and that retain biological activity, as measured by the ability to activate mammalian sperm, are considered as embodiments of the invention.

According to an embodiment of the invention, the La-1-like peptide agent comprises a C terminal truncation of the peptide SEQ ID NO. 1 or SEQ ID NO. 3 that is biologically active, as measured by its ability to activate mammalian sperm.

According to a preferred embodiment of the invention, the La-1-like peptide agent comprises the peptide according to SEQ ID NO. 1.

According to another embodiment, the La-1-like peptide agent comprises the peptide according to SEQ ID NO. 1 and/or SEQ ID NO. 3.

The peptide according to SEQ ID NO. 1 or SEQ ID NO. 3 may be labelled, for example, with a histidine tag or other labelling tag used to label proteins. According to an embodiment of the invention, the La-1-like peptide agent comprises peptides according to SEQ ID NO. 1 that are labelled. Similarly, truncations of SEQ ID NO. 3, including SEQ ID NO. 1, may be labelled and the La-1-like peptide agent may comprise such labelled truncations.

Figure 1B:
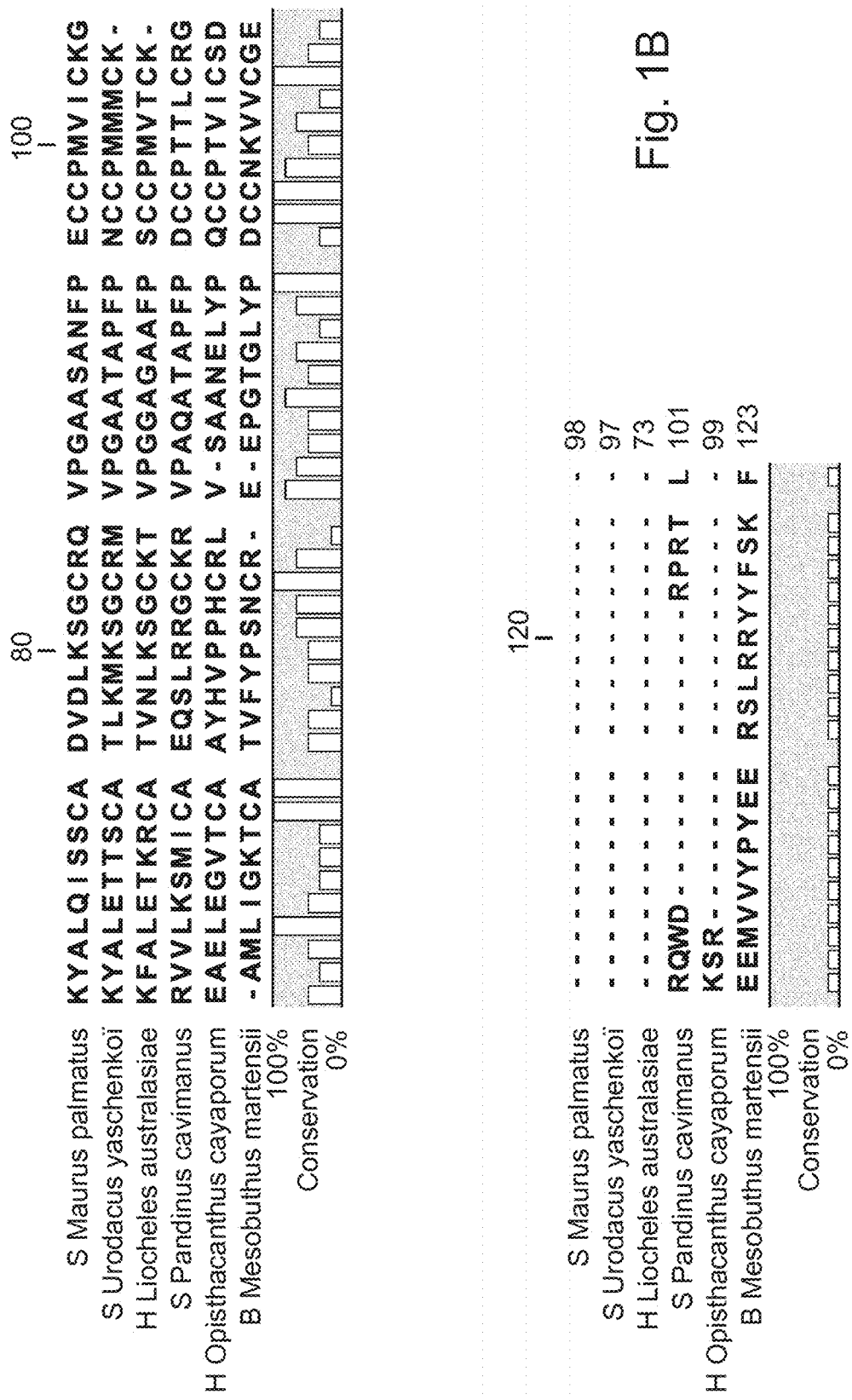

FIG. 1 shows the sequence alignment of the identified peptide, La-1-like protein from *S. Maurus palmatus* with five other species-*S. Urodacus yaschenkoï, H. Liocheles australasiae, S. Pandinus cavimanus, H. Opisthacanthus cayaporum* and *B. Mesobuthus martensii*. The consensus sequence is indicated at the bottom line in letters without colour and the % identity is indicated for each amino acid.

Peptides having at least 60%, or 70%, or 80%, or 90%, or 95% amino acid sequence identity with SEQ ID NO. 1 are expected to have the biological activity identified for the peptide SEQ ID NO. 1. These peptides are also considered capable of activating the motility of mammalian sperm, and are therefore considered as embodiments of the La-1-like peptide agent of the present invention. It is expected that the La-1-like peptide from, for example, *S. Urodacus yaschenkoï* (Luna-Ramirez, K., Quintero-Hernandez, V., Vargas-Jaimes, L., Batista, C. V., Winkel, K. D., and Possani, L. D. (2013). Characterization of the venom from the Australian scorpion *Urodacus yaschenkoi*: Molecular mass analysis of components, cDNA sequences and peptides with antimicrobial activity. Toxicon. 63:44-54. doi: 10.1016/j.toxicon.2012.11.017. Epub@2012 Nov. 23., 44-54), *H. Liocheles australasiae* (Miyashita, M., Otsuki, J., Hanai, Y., Nakagawa, Y., and Miyagawa, H. (2007). Characterization of peptide components in the venom of the scorpion *Liocheles australasiae* (Hemiscorpiidae). Toxicon. 50, 428-437.), *S. Pandinus cavimanus* (Diego-Garcia, E., Peigneur, S., Clynen, E., Marien, T., Czech, L., Schoofs, L., and Tytgat, J. (2012). Molecular diversity of the telson and venom components from *Pandinus cavimanus* (Scorpionidae Latreille 1802): transcriptome, venomics and function. Proteomics. 12, 313-328), *H. Opisthacanthus cayaporum* (Silva, E. C., Camargos, T. S., Maranhao, A. Q., Silva-Pereira, I., Silva, L. P., Possani, L. D., and Schwartz, E. F. (2009). Cloning and characterization of cDNA sequences encoding for new venom peptides of the Brazilian scorpion *Opisthacanthus cayaporum*. Toxicon. 54, 252-261) and *B. Mesobuthus martensii* (Ma, Y., He, Y., Zhao, R., Wu, Y., Li, W., and Cao, Z. (2012). Extreme diversity of scorpion venom peptides and proteins revealed by transcriptomic analysis: implication for proteome evolution of scorpion venom arsenal. J. Proteomics. 75, 1563-1576) also activate the motility of mammalian sperm. A La-1-like peptide agent comprising any one or more of these peptides from the latter species is also considered as an embodiment of the invention.

According to an embodiment of the invention, the motility activating agent comprises at least one peptide having at least 60%, or 70%, or 80%, or 90%, or 95% amino acid sequence identity with SEQ ID NO. 1. The La-1-like peptide agent may be a biologically active N- and C terminal truncation or mutant of SEQ ID NO. 1 or of a peptide having at least 60%, or 70%, or 80%, or 90%, or 95% amino acid sequence identity with SEQ ID NO 1. The agent may comprise a mixture of any of said peptides. The peptides may be mutated to modulate their biological activity, for example by increasing it further, or increasing the duration of the biological effect or by altering another pharmacological parameter. Such peptides are considered part of the invention.

According to an embodiment of the invention, the peptides included in the activating agent are isolated from their natural sources. For example, the peptide according to SEQ ID NO. 1 may be isolated from Scorpion *Maurus palmatus*. For example, La-1-like peptide from other species including for example, *U. yaschenkoï*, *L. australasiae*, *P. cavimanus* and *M. martensii* may be isolated from their natural sources.

According to an embodiment of the invention, the peptide comprised in the La-1-like peptide agent is a recombinant peptide produced in a suitable expression system, for example, in yeast, *E. coli*, or another suitable expression system.

According to a preferred embodiment of the invention, the La-1-like peptide agent is SEQ ID NO. 1 or SEQ ID NO. 3, or a homologous peptide produced in a suitable expressive system, for example, *E. Coli* or Sf9 cells.

In an embodiment of the invention, the La-1-like peptide agent may comprise hybrid or fusion peptides of SEQ ID NO. 1 or of homologous peptides, fused to another peptide sequence. The other peptide sequence may have a function that helps the fertilisation process, or stabilizes the La-1-like peptide agent.

The inventors have synthesized the peptide according to SEQ ID NO. 1 using Native Chemical Ligation Strategy and have confirmed that it retains the biological activity associated with the peptide isolated from the venom of Scorpion *Maurus palmatus*.

According to an embodiment of the invention, the La-1-like peptide agent is a synthetic peptide produced by a suitable synthetic method known to the skilled person. For example, one may cite Native Chemical Ligation Strategy.

According to a preferred embodiment of the invention, the La-1-like peptide agent may comprise a synthetic peptide according to SEQ ID NO. 1, or a homologous peptide.

According to an embodiment of the invention, the La-1-like peptide agent may comprise a peptide that is a synthetic derivative of SEQ ID NO. 1 or of homologous peptides as described above. These derivatives may include derivatives that are useful to increase stability or improve other physicochemical or pharmacokinetic or pharmacodynamic parameters, for example, PEGylation, hyperglycosylation, or mannosylation According to an embodiment of the invention, the La-1-like peptide agent may comprise peptides that have been produced synthetically and/or peptides that have been produced by recombinant expression systems and/or peptides that have been isolated from natural sources.

In a preferred embodiment, the La-1-like peptide agent comprises SEQ ID NO. 1 or homologous peptides that have been isolated from at least one natural source, for example from *Maurus palmatus* venom. In another embodiment, the La-1-like peptide agent comprises recombinant SEQ ID NO. 1 or homologous peptides that have been expressed in a suitable expression system. In a preferred embodiment, the La-1-like peptide agent comprises SEQ ID NO. 1 or homologous peptides that have been chemically synthesized. In another embodiment, the La-1-like peptide agent comprises a mixture of the aforementioned peptides.

According to an embodiment of the invention, the La-1-like peptide agent may comprise peptides that are in dimeric or trimeric or multimeric form, as long as they retain their biological activity.

The La-1-like peptide agent may be stored in suitable buffers for immediate use or for storage at approximately 4° C. According to one embodiment, the La-1-like peptide agent may be frozen. In that case, the La-1-like peptide agent may be stored in a suitable cryogenic buffer. If frozen, the La-1-like peptide agent may be stored at −20° C. for up to approximately 6 months or for longer periods at −80° C.

The La-1-like peptide agent, when in the form of a solution, or milk, or suspension, or gel, may be sterilised using any method suitable for sterilizing peptides, for example by filtration with 0.22 μm filter.

According to an embodiment of the invention, the La-1-like peptide agent may be lyophilized and stored at room temperature or 4° C., or −20° C., or −80° C., depending on the needs of the user.

According to an embodiment of the invention, the La-1-like peptide agent may be stored in the form of a powder, fibre, flakes, a suspension, solution, or any other suitable form.

According to another aspect of the invention, the motility activating agent may be combined with at least one other agent useful in ART procedures, including an in vitro fertilisation procedure or in an in vivo assisted reproduction procedure. This other agent may be an agent useful for the increasing in sperm motility, stabilizing the sperm sample or any other function useful in ART techniques.

La-1-Like Peptide Agent has Biological Activity

The La-1-like peptide agent of the invention is of therapeutic use because of its newly identified biological activity. In one embodiment of the invention, the La-1-like peptide agent may be used as a medicament.

Accordingly, the present invention also provides pharmaceutical compositions comprising, as an active ingredient, the La-1-like peptide agent, in association with a pharmaceutical carrier or diluent. The La-1-like peptide agent according to an embodiment of the invention may be administered by routes that allow the agent to come into contact with sperm. For example, according to an embodiment of the invention, the La-1-like peptide agent is administered to females by the vaginal route. In this case, the La-1-like peptide agent may be formulated in dosage forms appropriate for each route of administration.

Compositions containing the La-1-like peptide agent for vaginal administration may be in any suitable form, including creams or gels, preferably in the form of a suppository. These forms may contain, in addition to the active peptide, suitable excipients, known to the skilled person.

Compositions may be administered to humans or to animals. The compositions may be in the form of a solution, suspension, gel, cream, milk, capsule, tablet and/or other suitable forms for administration to humans or animals.

According to an embodiment of the invention, the La-1-like peptide agent may be used for the treatment of male infertility in mammals, particularly in humans.

According to an embodiment of the invention, the La-1-like peptide agent may be used for the treatment of asthenozoospermia and/or oligozoospermia.

The applicant has demonstrated the biological activity of the peptide according to SEQ ID NO. 1 (see Examples 2, 3 and 4).

In Example 2, samples of human sperm were incubated with solutions of the peptide according to SEQ ID NO. 1. The results shown in FIG. 2B demonstrate an increase in sperm motility after incubation. Furthermore, the slower the spermatozoa were initially, the more effective the peptide was in increasing their velocity. The upper left-hand panel shows that the sperm having a low initial track speed (PV units) had higher motility activation compared to those with higher initial track speeds (the CL). Similarly, in the upper right panel, the sperm having low initial path velocity (VAP) experienced increases of up to 80%, while those having an initial VAP of 60 μm/s had about 20% increase in motility.

Figure 2A:
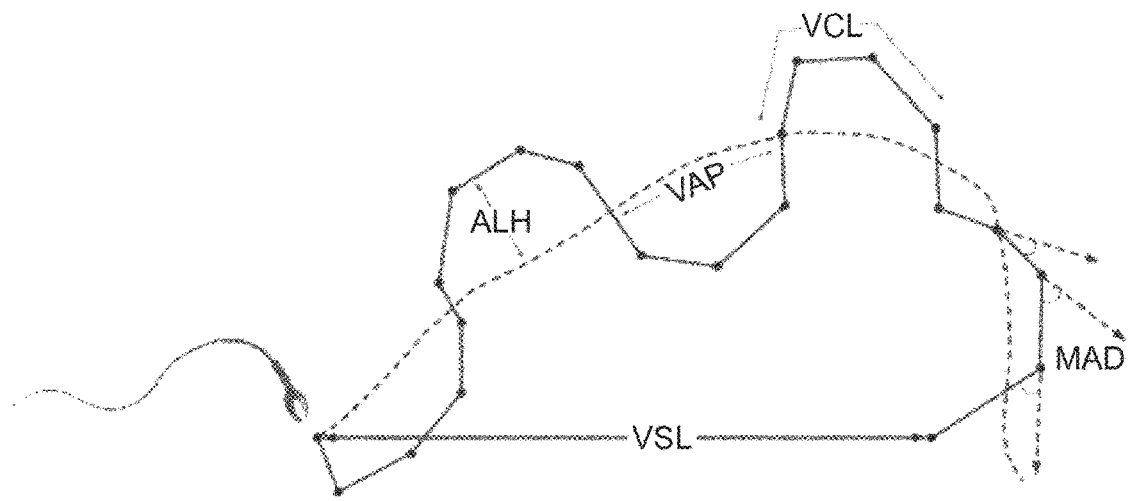
FIG. 2A: Diagram showing definitions of sperm motion.
 VCL: Curvilinear velocity is the average velocity of the sperm head through its real path.
 VAP: Average path velocity is the average velocity of the sperm head through its average trajectory.
 ALH: Lateral Displacement Of Sperm Head (ALH) is defined as the amplitude of the variations of the current path of the sperm head in relation to the VAP.
 VSL: Straight line velocity is the average velocity of the sperm head through a straight line connecting the first position to its last position.
Figure 2B:
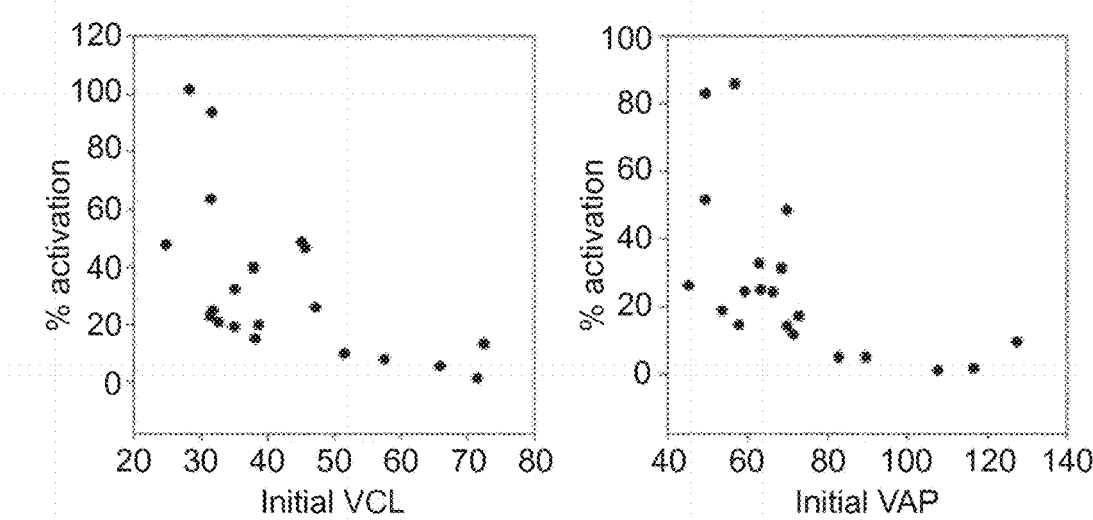
FIG. 2B: Results of the velocity test performed on human spermatazoa treated with the peptide SEQ ID NO 1.
 A: % activation with respect to initial VCL.
 B: % activation with respect to initial VAP.
 C: % activation with respect to initial ALH.
 D: % activation with respect to initial VSL.

The bottom left-hand panel of FIG. 2B shows the results of a test, where the effect of incubation with the peptide according to SEQ ID NO. 1 on human sperm lateral amplitude (ALH, see FIG. 2A) was measured. The percentage increase is noted on the Y axis. Those sperm having an initial lateral amplitude of less than 3.5 μm had greater increases than those with higher initial ALH values. In the bottom right-hand panel, the effect of the peptide on progressive velocity (VSL) was measured. Those sperm having an initial progress of velocity of less than 30 μm/s showed an increase of between 20 and nearly 120%, with just one outlier. Those with an initial VSL of about 40 μm/s showed an increase of between 20 and 55%, whereas those with an initial VSL of more than 60 μm/s showed a 5 to 20% increase due to the incubation with the peptide.

According to one embodiment of the invention, the La-1-like peptide agent increases mammalian sperm motility as measured using at least one of following parameters: track speed, path velocity, natural amplitude, non-progressive velocity and progressive velocity.

According to one embodiment of the invention, the La-1-like peptide agent is particularly effective for the treatment of asthenozoospermia. According to one embodiment of the invention, the La-1-like peptide agent increases the progressive motility (initial velocity of more than 30 μm/s) of mammalian spermatozoa. In a preferred embodiment, the agent increases the non-progressive motility (initial velocity of between 1 and 30 μm/s) of mammalian spermatozoa.

In certain artificial reproduction techniques, such as in vitro fertilization (IVF), in particular, intra-cytoplasmic sperm injection (ICSI), it is desirable to treat the sperm to be used with an agent to activate the motility of the sperm. This procedure may also be used in artificial insemination techniques, including IUI. This treatment may comprise the step of incubating the sperm sample to be used with an activating agent.

According to one embodiment of the invention, the La-1-like peptide agent may be incubated with sperm samples to be used in artificial reproduction techniques, including IVF, in particular ICSI.

According to an embodiment of the invention, the La-1-like peptide agent may be incubated with sperm samples to be used in artificial insemination methods, for example IUI. In an embodiment of the invention, the artificial insemination may be carried out for therapeutic purposes, in humans and/or animals.

In one embodiment of the invention, the artificial insemination may be carried out for non-therapeutic purposes in animals. In this case, the use of the La-1-like peptide agent may be used to increase the animals' fertility and/or to increase the fertilization rate obtained in artificial procedures.

According to an embodiment of the invention, the incubation of the La-1-like peptide agent with the sperm sample may be carried out according to methods known to the skilled person.

The peptide to be used may be present in a suitable solution, for example in medium supporting sperm survival or capacitation. The final concentration of the peptide (after it has been mixed with sperm) may be in the range 0.01 micromolar to 1 micromolar (μM). According to a preferred embodiment of the invention, for bovine sperm, a concentration of 0.1 μM is preferred.

In general, a quantity of the sperm solution/suspension may be added to a suitable container containing the sperm to be treated. For example, to treat 1 million cells in 1 milliter of sperm medium, a quantity of La-1 like peptide agent in the range of 0.1 to 0.2 nanomoles may be added. The sperm cells may be present in a suitable buffer, for example medium known to allow sperm survival. One may cite, for example talp medium for bovine sperm, M2 medium for mouse sperm, synthetic human fluid (HTF) for human sperm or any sperm medium allowing sperm survival for example, as described in Fraser LR (1993) In vitro capacitation and fertilization. Methods in enzymology 225, p. 239-253.

According to one embodiment of the invention, for the treatment of bovine sperm in, for example, an IUI method, a final concentration of La-1 like peptide agent of 0.1 μm is preferred. The incubation time may vary from 1 minute to 20 minutes, preferably 5 minutes to 15 minutes, more preferably 8 minutes to 10 minutes. The incubation time may, of course, vary according to the temperature used and the concentration rate of La-1 like peptide agent used and other factors, but the skilled person can easily determine suitable incubation conditions to be used.

According to one embodiment of the invention, the incubation temperature may vary from 35° C. to 39° C., for example 38° C.

During and/or following incubation with the motility activating agent, the increase in sperm motility may be measured by observing the sperm sample under a microscope or another means of observation, or by using a cell sorting machine or other apparatus that allows one to measure cell motility. This allows the selection of the spermatozoa in the sample for further use in the ART procedure.

According to an embodiment of the invention, sperm motility is measured as any one or more of the following parameters track speed, path velocity, natural amplitude, non-progressive velocity and progressive velocity. Preferred parameters are non-progressive velocity and progressive velocity.

According to an embodiment of the invention, the most motile spermatozoa in the spermatozoa sample may be selected for use in the given procedure. For example, the 10%, or 20%, or 30%, or 40%, or 50% most motile sperm may be selected. Preferably, the 50% most motile of the spermatozoa are selected.

The number of spermatozoa selected will depend on the fertilization technique being used.

For example, for ICSI, the single most motile sperm cell is used for introduction into the ovum.

In IVF techniques where the mammalian ovum is incubated with a number of spermatozoa, a suitable number of spermatozoa are chosen.

In artificial insemination techniques, for example, in IUI, substantially all of the sperm cells may be used, or at least 50%, or at least 60%, or at least 70%, or at least 80%, or least 90% of the sperm cells may be used.

Alternatively, no selection is made, and all, or substantially all, of the sperm sample is used in the procedure. This may be the case, for example, in the use of industrial artificial insemination techniques to be used on animals. In this case, the La-1-like peptide agent is used to increase the fertility of the male animal. This leads to an increase in the fertilization rate obtained in the procedure.

The La-1-like peptide agent according to various embodiments of invention may be used to activate the motility of mammalian sperm. Preferred species include human, bovine, porcine, goat, sheep, dogs and cats.

According to another embodiment of the invention, the La-1-like peptide agent is used to increase the fertilization rate in an artificial reproduction technique in animals. Preferred animals are bovine, ovine and porcine.

For all of the techniques mentioned, where the sperm are incubated in vitro with the La-1-like peptide agent, the latter agent may optionally be removed before the sperm sample is introduced into the female mammal.

Example 3 demonstrates that the La-1-like peptide agent according to one embodiment of the invention, comprising the peptide according to SEQ ID NO. 1, increases the rate of fertilization in a mouse in vitro fertilization experiment. The rate of fertilization was measured according to the number of mice embryos at the two cell stage. The results indicate that in the presence of the La-1-like peptide agent, the rate of fertilization was increased by approximately 20% compared to the control. These data also indicate that the La-1-like peptide agent is not toxic and does not prevent embryo development.

According to an embodiment of the invention, the La-1-like peptide agent increases the rate of fertilization in an in vitro fertilization procedure, in particular, ICSI. In particular, the ICSI is carried out in humans.

According to an embodiment of the invention, the La-1-like peptide agent increases the rate of fertilization in an artificial insemination procedure, in particular IUI. The IUI may be carried out in humans or animals for therapeutic reasons to treat male infertility.

In some infertile males, the sperm maturation process that takes place in the epididymis is dysfunctional and it is desirable to stimulate the maturation process in an in vitro treatment on the sperm, which have been taken from the testes. Once the spermatozoa have undergone maturation, they may be then used for in vitro fertilization procedures.

Figure 3:
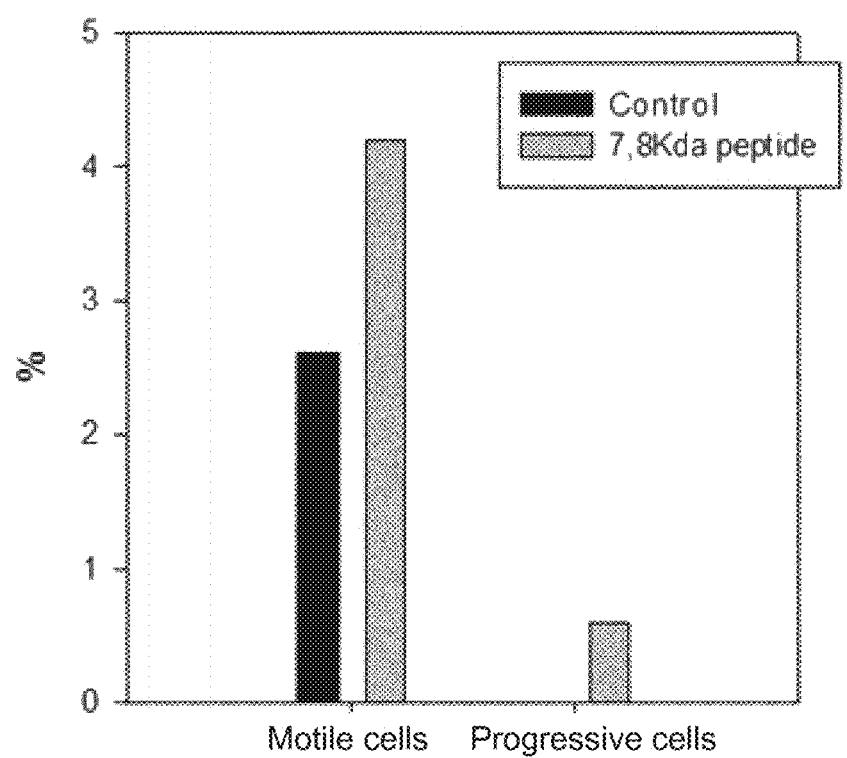
FIG. 3: Measurement of motile cells and progressive cells after incubation of testicular sperm from macaca (non-human primate) with (7.8 Kda peptide) and without (Control) peptide SEQ ID NO. 1. Motile sperm and progressive sperm were characterized by VAP>1 µm/s and VAP>30 µm/s and STR>70%, respectively. STR=VSL/VAP. Statistical analyses were performed with SigmaPlot. t tests were used to compare the effects of La1-like peptide on sperm motility parameters. Data represent mean±SEM. Statistical tests with a 2-tailed P values 0.05 were considered significant.
Figure 4:
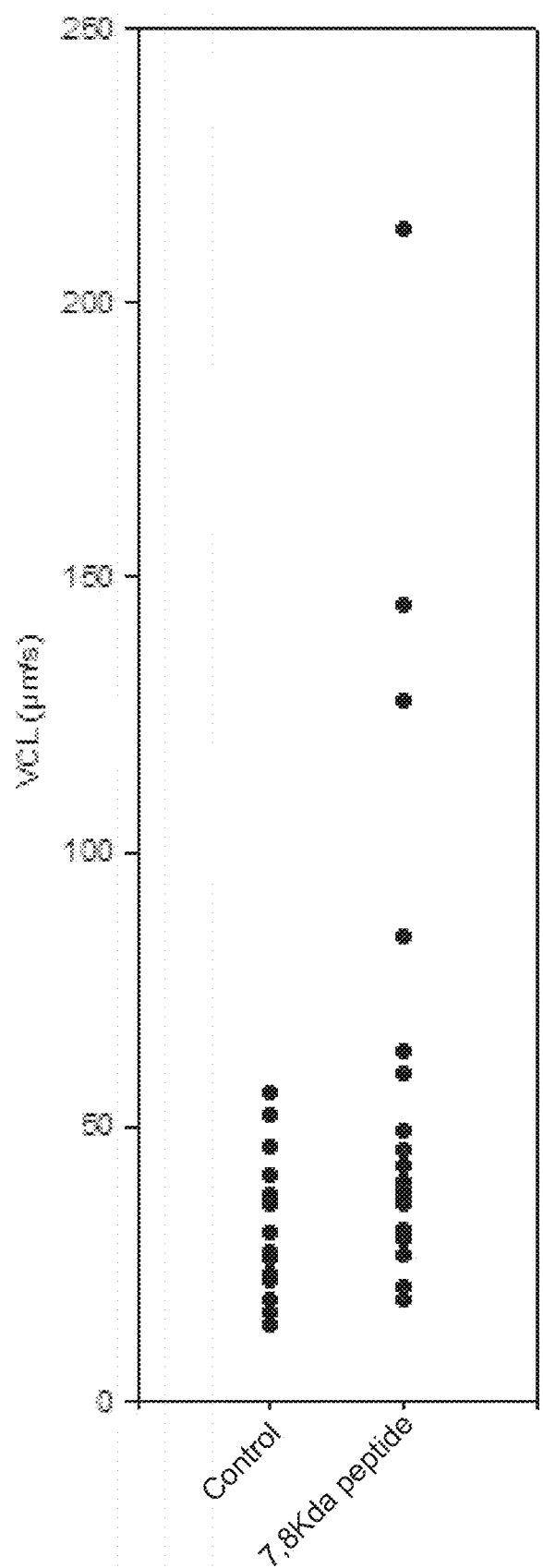
FIG. 4: Measurement of the velocity, VCL (µm/s) of testicular sperm from non-human primates with (7.8 Kda peptide) and without (Control) incubation with peptide SEQ ID NO 1. Motile sperm and progressive sperm were characterized by VAP>1 µm/s and VAP>30 µm/s and STR>70%, respectively. STR=VSL/VAP. Statistical analyses were performed with SigmaPlot. t tests were used to compare the effects of La1-like peptide on sperm motility parameters. Data represent mean±SEM. Statistical tests with a 2-tailed P values≤0.05 were considered significant.

Example 4 describes how the incubation of the peptide according to SEQ NO.1 with non-human primate testicular sperm leads to an increase of both the non-progressive velocity and progressive velocity of the sperm cells in the sample. The results are shown in FIGS. 3 and 4. The increase of motility in these testicular sperm cells is comparable to that occurring in the maturation process that normally occurs in the epididymis.

Testicular spermatazoa that have demonstrated increased motility after treatment with the La-1-like peptide agent, according to an embodiment of the invention, may be then selected for use in an IVF procedure, for example an ICSI procedure. According to an embodiment of the invention, a sample of La-1-like peptide agent may be incubated with a testicular sperm sample. The agent is used at a suitable concentration for example 0.01 micromolar to 1 micromolar. The sperm samples are used in suitable concentrations for example, 1 million/ml. For example, to treat 1 million of cells in 1 milliter of sperm medium, a quantity in the range of 0.1 to 0.2 nanomoles may be added.

The testicular sperm sample may be present in a suitable buffer. The activation agent is, in general, stored in a suitable buffer. The incubation period may be from 1 minutes to 20 minutes and is monitored either visually by microscope or other viewing means or by other means including using a cell sorting machine.

In another embodiment of the invention, the activating agent is used to increase the motility of sperm in a sperm sample from the epididymis. In this case, the same or a similar protocol may be used as those described above.

The increase in motility of the sperm cells may be monitored during and/or after incubation with the La-1-like peptide agent. The increase in motility may be measured by using one or more of the following parameters: track speed, path velocity, natural amplitude, non-progressive velocity and progressive velocity.

In one embodiment of the invention, the La-1-like peptide agent is used to increase the motility of sperm in an ejaculated sperm sample.

In one embodiment of the invention, the La-1-like peptide agent is used to increase the motility of a sperm sample which has been previously frozen. The sperm sample may be an ejaculated sample or one that has been taken from the epididymis or from the testes.

Figure 5:
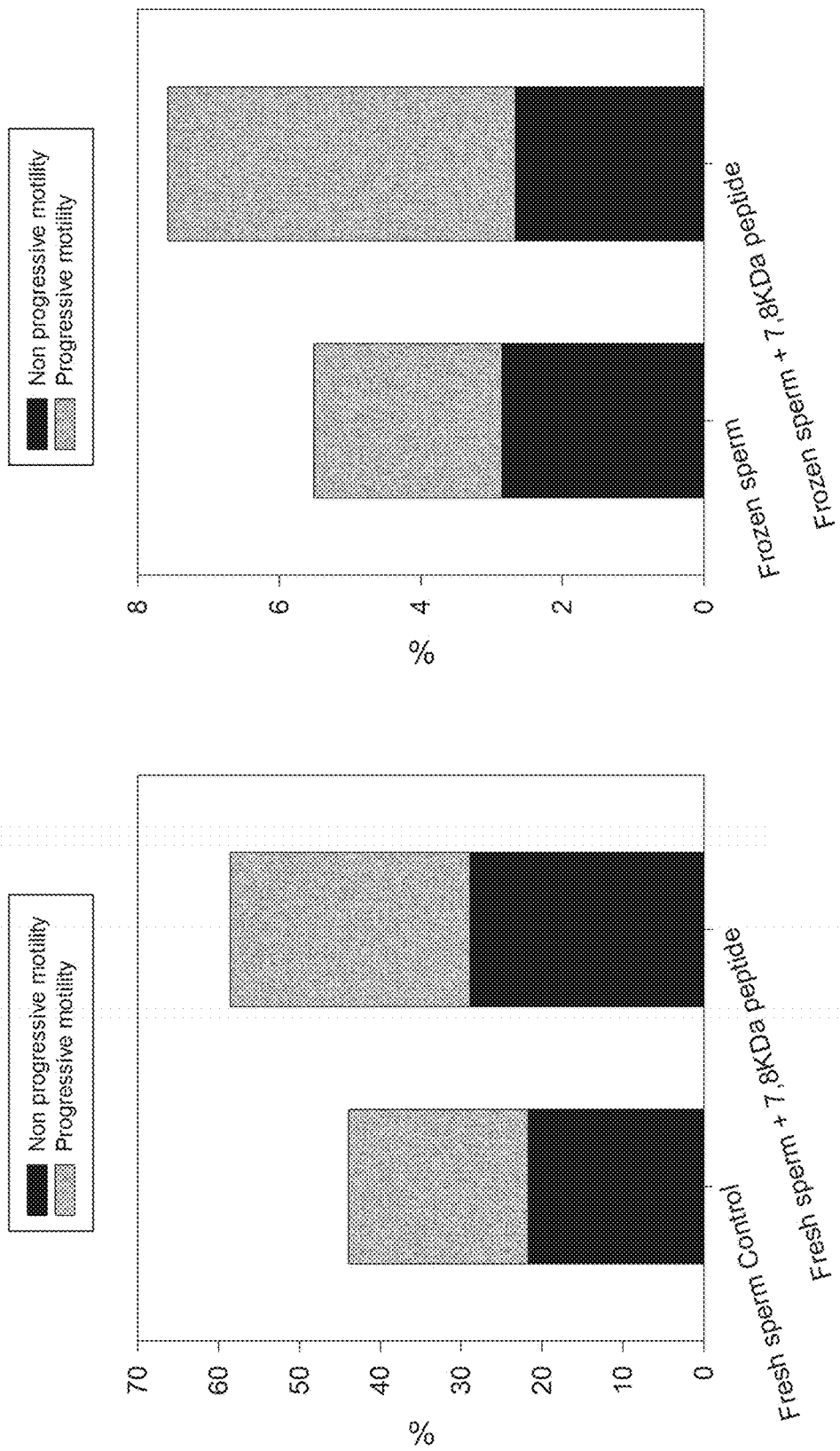
FIG. 5: Measurement of % motile cells and progressive cells after incubation of fresh (left hand panel) and frozen (right hand panel) human ejaculated sperm with (7.8 kDa peptide) or without (Control) the peptide according to SEQ ID NO. 1. Motile sperm and progressive sperm were characterized by VAP>1 µm/s and VAP>30 µm/s and STR>70%, respectively. STR=VSL/VAP. Statistical analyses were performed with SigmaPlot. t tests were used to compare the effects of La1-like peptide on sperm motility parameters. Data represent mean±SEM. Statistical tests with a 2-tailed P values≤0.05 were considered significant.

This is particularly relevant in artificial reproductive techniques, where often sperm samples are frozen and kept for later use. It is known that freezing sperm samples often reduces their motility. In Example 5, human fresh and frozen sperm samples were incubated with the peptide according to SEQ ID NO. 1. The progressive and non-progressive motility of the samples was measured. The results, which are shown in FIG. 5, indicate that incubation with the La-1-like peptide agent increases the progressive motility as well as the non-progressive motility in both fresh sperm samples (left-hand panel) and frozen samples (right-hand panel). The data also suggests that the effect is greater for the frozen samples than for the fresh samples.

The activating agent may also be brought into contact with the sperm in vivo. In this case, the activating agent may be administered locally in the vagina or cervix of the female before insemination takes place.

In one embodiment of the invention, the motility activating agent is in the form of a gel, capsule, milk or cream or other form suitable for local administration to the vaginal tract and/or cervical area of the female. The motility activating agent may be thus administered locally to the female in the vaginal or cervical area. Thus, when the female is inseminated, the sperm comes into contact with the activating agent.

In an embodiment of the invention, the La-1-like peptide agent may be present with other agents that may be those usually present in medium or buffer used to stabilize the cells and peptide agent respectively.

According to one embodiment of the invention, the La-1-like peptide agent may be present with other known agents that may facilitate fertilisation, such as for example, Papaverine or other agents. These additional agents may be present when the La-1-like peptide agent is being used for artificial insemination procedures or when it is being used for natural insemination.

In an embodiment of the invention, the La-1-like peptide agent is used for artificial insemination methods, for example, IUI. These methods are also the subject of the invention. IUI may be carried out in animals for industrial purposes. In this case, the La-1-like peptide agent is used to increase the fertility of the animals. The artificial insemination procedure may be carried out by the methods known to the skilled person.

For example, the sperm to be used in the insemination may be brought into contact with the La-1-like peptide agent in vitro before the insemination takes place. In this case, both the La-1-like peptide agent and the sperm are incubated in a suitable container, or syringe. The sperm may be present either as semen or in a suitable medium buffer. The sperm mobility activating agent may be present in a suitable buffer.

The La-1-like peptide agent may be introduced within the sperm straw, before freezing. According to another embodiment of the invention, during an artificial insemination procedure, the La-1-like peptide is co-injected with the sperm.

According to another embodiment of the invention, during an artificial insemination procedure, the sperm and the La-1-like peptide agent may be incubated together for a certain period of time for example 1 to 20 minutes, preferably, from 5 to 15 minutes, before injection into the female mammal.

The sperm and the La-1-like peptide agent may also be mixed together without a specific incubation step just before insemination.

For the insemination, the sperm and La-1-like peptide agent may be injected into the vaginal tract or cervical area of the female. Animals that may be used in these methods include bovine, ovine, equine, cats and dogs, birds, for example chickens, turkeys and other birds that are produced industrially.

The La-1-like peptide agent increases the fertilization rate of the procedure. This has a huge time and cost benefit for the user, allowing him to reduce the number of interventions made per offspring obtained.

In one aspect, the invention is a method for increasing the fertilization rate in an artificial insemination procedure in an animal. The method comprises the steps of:
  a) bringing into contact a sperm sample from an animal with a therapeutically effective amount of the La-1-like peptide agent comprising SEQ ID NO. 1;
  b) optionally removing the La-1-like peptide agent;
  c) artificially inseminating the female animal with said sperm sample and if present, the La-1-like peptide agent;
  d) measuring the fertility rate.

The following are examples that illustrate the biological effect of the sperm motility agent and are by no way limiting.

Example 1

Venom Separation and La-1 Like Peptide Isolation
Venom Origin

Crude venom from *Maurus palmatus* was obtained from Alphabiotoxine Laboratory (Montroeul-au-bois, BELGIUM) or Venomtech (Sandwich, Kent, UK). Ten mg of lyophilized crude venom was dissolved in 500 μL of 100 mM ammonium acetate pH 6.8 and centrifuged at 10,000 g for 10 min. Two hundred fifty microliter of supernatant was used for further purifications.

Purification by Size Exclusion Ehromatography (SEC)

Separation was performed on a Superdex_peptide 10/300 GL gel filtration column, with elution at 0.5 mL/min in 100 mM ammonium acetate, pH 6.8. Fractions were collected every minute and the absorbance was monitored at 225 nm. The fractions were kept at −20° C. until bioactivity screening and mass spectrometry analysis was carried out.

Purification of La-1-Like Peptide from Crude Venom of *M. palmatus*

Prepurification by Solid Phase Extraction (SPE)

The crude lyophilized venom from *M. palmatus* (2 mg) was dissolved in 200 uL of 0.1% trifluoroacetic acid (0.1% TFA) and prepurified onto two serially linked SepPak C18 Light (Waters Corporation, Milford, Mass.), following the manufacturer's instructions and eluted with 3 mL 80% acetonitrile (ACN) in 0.1% TFA. The 80% eluted fraction was dried under vaccum using a speed-vacuum system (Labconco, Freezone 2.5plus, Kansas City, Mo.) and suspended in 0.1% TFA.

Analysis by On Line Liquid Chromatography Coupled to Electrospray Ionization Tandem Mass Spectrometry (LC-ESI-MS/MS)

A fraction aliquot of an equivalent of 200 μg of crude venom was injected for on line LC-ESI-MS/MS analysis on an Agilent HPLC HP-1290 system (Agilent Technologies, Santa Clara, Calif.). Separation was performed on an Accucore $C_{18}$ column (2.1 mm×150 mm from Thermo Scientific, Bremen, Germany), maintained at 35° C., and on-line coupled to a Thermo Q-Exactive Orbitrap. Solvent A was 0.1% formic acid and B was acetonitrile in 0.1% formic acid. A linear gradient, starting from 4% B to 60% B for 120 min at a flow rate of 350 μL/min was applied to fractionate the venom components. The high-resolution mass spectrometer was operated in positive polarity and data-dependent mode. The Q-Exactive Orbitrap acquired a full-range scan from 380 to 2000 Th (70,000 resolution, AGC target 3.106, maximum IT 200 ms) and then fragmented the top ten peptide ions in each cycle (17,500 resolution, AGC target 105, maximum IT 100 ms, intensity threshold 2×104, excluding charge-unassigned ions, Normalized Collision Energy selected at 27. Parent ions were then excluded from MS/MS for the next 15 s. The software Chemstation B.04.03 and Xcalibur™ 2.2 were used to control the HPLC and the mass spectrometer, respectively.

Isolation of Native La-1-Like Peptide by Reversed Phase HPLC

To isolate the bioactive fraction, an equivalent of 1.7 mg of crude venom was injected using an Agilent HPLC HP-1290 system in the same conditions of elution as detailed above. Fractions were hand-collected following the absorbance monitored at 225 nm, dried under vacuum and kept dried until use.

Example 2

Velocity Test Performed on Human Spermatazoa Treated with the Peptide SEQ ID NO. 1

Human sperm were obtained from patient consulting at the fertility department of Grenoble, following approval by the ethical committee and informed consent from the patients. All patients gave an informed consent for the conservation of the remnant sperm in the Germetheque biobank and their use in studies on human fertility in accordance with the Helsinki Declaration of 1975 on human experimentation. The Germetheque Scientific Committee approved the present study design. Ejaculate was liquefied at 37° C. for 30 min and sperm were washed twice in Sperm Preparation Medium (Origio, Målov, Denmark) at 500 g for 5 min. Concentration is then adjusted for CASA analysis. Sperm were also frozen with SpermFreeze (Fertipro NV, Beernem, Belgium) for further analysis as frozen sperm.

Computer-Assisted Motility Analysis (CASA)

After 10 minutes incubation with the peptide according to SEQ ID NO. 1 (natural, or synthesized), the sperm suspension was immediately placed onto an analysis chamber (Leja Products B.V., Netherlands) of 100 μm depth for mouse sperm and 20 μm depth for human, NHP and bovine sperm, and kept at 37° C. for microscopic quantitative study of sperm movement. Sperm motility parameters were measured at 37° C. using a sperm analyzer (Hamilton Thorn Research, Beverley). The settings employed for analysis were as follows for human, NHP, bovine and mouse respectively: acquisition rate (60;60;60;60) Hz; number of frames: (30;20;30;45); minimum contrast: (80;80;80;50); minimum cell size: (3;4;5;5); low static-size gate: (0,85;0,79;0,1;0,3); high static-size gate: (4,24;2,52;3,4;1,95); low static-intensity gate: (0,39;0,62;0,3;0,5); high static-intensity gate: (1,4; 1,4;1,7;1,3); minimum elongation gate: (0;2;8;0); maximum elongation gate: (85;50;97;87); magnification factor: (1,89;

1,89;1,89;0,7). The motility parameters measured were curvilinear velocity (VCL) and amplitude of lateral head displacement (ALH). A minimum of 100 motile spermatozoa was analyzed for each assay. Motile sperm were defined by VAP>(1;1;1;1) and progressive sperm were defined by VAP>(25;25;50;30) and STR>(80;80;70;70).

Measurement of Sperm Vitality

Forty μL of sperm were mixed with 20 μL of eosin 1% diluted in NaCl 9/1000 and 20 μL of nigrosine 10% diluted in NaCl 9/1000. Sperm were then layered onto glass slide and dried. A minimum of 100 spermatozoa was analyzed for each assay.

Data are shown in FIG. 2.

Example 3

Fertilization Study in Mice

Eggs were collected from mature OF1 females, synchronized with 5 units of pregnant mare serum gonadotrophin (PMSG) and 5 units of human chorionic gonadotrophin (hCG). Sperm were capacitated for 55 minutes in M16 2% BSA (37° C., 5% $CO_2$) and introduced into droplets containing oocytes. The active peptide was introduced into droplets at the same time. Oocytes were incubated with $1.5 \times 10^5$ to $5 \times 10^5$ capacitated sperm/ml (37° C., 5% $CO_2$) in M16 medium and unbound sperm were washed away after 4 hours incubation. Twenty-four hours after fertilization, the different stages, i.e. unfertilized oocytes (including aborted embryos and corresponding to fragmented oocytes or oocytes blocked after the extrusion of the second polar body) and 2-cell embryos (as an indication of successful fertilization) were scored.

Example 4

Motility Activation in Testicular Sperm from Macaca

Macaca testes were collected after euthanasia. Seminiferous tubules were torn up by manual trituration in DMEM with a high glucose concentration. A swim-up was performed at 37° C. for 30 min and the upper fraction was washed twice with DMEM high glucose. The sperm concentration was adjusted for Computer assisted sperm analysis (CASA). After ten minutes incubation with La-1-like peptide according to SEQ ID NO. 1, sperm motility was measured using the same conditions as those in Example 2.

SEQUENCE LISTING

SEQ ID NO. 1
S Maurus palmatus
Ser Gly Glu Ser Cys Lys Ala Gly Lys Phe Thr Val
Leu Val Gly His Gln Gln Asn Asp Lys Ser Thr Cys
Thr Leu Tyr Lys Cys Leu Asn Phe Lys Arg Lys Tyr
Ala Leu Gln Ile Ser Ser Cys Ala Asp Val Asp Leu
Lys Ser Gly Cys Arg Gln Val Pro Gly Ala Ala Ser
Ala Asn Phe Pro Glu Cys Cys Pro Met Val Ile Cys
Lys SEQ ID NO. 2
S Maurus palmatus
Met Glu His Ala Leu Lys Ser Leu Leu Leu Ile Cys
Leu Val Val Phe Ser Phe Thr Ser Leu Cys Met Gly SEQ ID NO. 3
S Maurus palmatus
Met Glu His Ala Leu Lys Ser Leu Leu Leu Ile Cys
Leu Val Val Phe Ser Phe Thr Ser Leu Cys Met Gly
Ser Gly Glu Ser Cys Lys Ala Gly Lys Phe Thr Val
Leu Val Gly His Gln Gln Asn Asp Lys Ser Thr Cys
Thr Leu Tyr Lys Cys Leu Asn Phe Lys Arg Lys Tyr Ala Leu Gln Ile Ser Ser Cys Ala Asp Val Asp Leu
Lys Ser Gly Cys Arg Gln Val Pro Gly Ala Ala Ser
Ala Asn Phe Pro Glu Cys Cys Pro Met Val Ile Cys
Lys Gly SEQ ID NO. 4
S Urodacus yaschenkoï
Met Glu Arg Ile Leu Lys Pro Val Phe Leu Ala Ile
Leu Ile Val Leu Ser Phe Ser Ser Gln Cys Met Gly
Phe Gly Glu Ser Cys Gln Ala Gly Lys His Ile Val
Pro Val Gly Gln Gln Gln Ile Asp Ser Ser Thr Cys
Thr Leu Tyr Lys Cys Ser Asn Tyr Asn Arg Lys Tyr
Ala Leu Glu Thr Thr Ser Cys Ala Thr Leu Lys Met
Lys Ser Gly Cys Arg Met Val Pro Gly Ala Ala Thr
Ala Pro Phe Pro Asn Cys Cys Pro Met Met Met Cys
Lys SEQ ID NO. 5
H Liocheles australasiae
Phe Gly Glu Ser Cys Ile Ala Gly Arg Phe Ile Val
Pro Leu Gly Gln Gln Val Thr Asp Gln Arg Asp Cys
Ala Leu Tyr Lys Cys Val Asn Tyr Asn Lys Lys Phe
Ala Leu Glu Thr Lys Arg Cys Ala Thr Val Asn Leu
Lys Ser Gly Cys Lys Thr Val Pro Gly Gly Ala Gly
Ala Ala Phe Pro Ser Cys Cys Pro Met Val Thr Cys
Lys SEQ ID NO. 6
S Pandinus cavimanus
Met Ser His Leu Arg Ile Ala Val Ile Phe Leu Cys
Thr Leu Phe Ala Leu Thr Ala Gly Ala Glu Glu Ser
Cys Gln Val Gly Gly Leu Thr Ile Pro Val Gly Lys
Thr Gln Gln Asp Arg Cys Thr Leu Tyr Glu Cys Thr
Met Glu Ser Asn Arg Val Val Leu Lys Ser Met Ile
Cys Ala Glu Gln Ser Leu Arg Arg Gly Cys Lys Arg
Val Pro Ala Gln Ala Thr Ala Pro Phe Pro Asp Cys
Cys Pro Thr Thr Leu Cys Arg Gly Arg Gln Trp Asp
Arg Pro Arg Thr Leu SEQ ID NO. 7
H Opisthacanthus cayaporum
Met Lys Ile Ala Cys Thr Leu Val Leu Phe Val Met
Leu Arg Cys Tyr Val Asn Ala Arg Asn Ile Pro Gly
Thr Cys Arg Thr His Thr Gly Ile Ile Leu Leu Ser
Gly Glu Glu Trp Lys Asp Pro Asn His Cys Ser Thr
Tyr Arg Cys Ser Arg Ile Phe Asp Gly Glu Ala Glu
Leu Glu Gly Val Thr Cys Ala Ala Tyr His Val Pro
Pro His Cys Arg Leu Val Ser Ala Ala Asn Glu Leu
Tyr Pro Gln Cys Cys Pro Thr Val Ile Cys Ser Asp
Lys Ser Arg SEQ ID NO. 8
B Mesobuthus martensii
Met Ser Ile Lys Ile Ser Ala Ile Ala Leu Phe Met
Leu Ser Phe Thr Val Phe Val Asn Gly Ile Pro Phe
Phe Leu Thr Lys Gly Arg Ile Asp Thr Cys Lys Thr
Leu Thr Gly Glu Thr Ile Lys Ile Gly Glu Ser Trp
His Asp Pro Asn Ser Cys Ser Val Tyr Tyr Cys Glu
Val Asn Ser Leu Gly Ala Met Leu Ile Gly Lys Thr
Cys Ala Thr Val Phe Tyr Pro Ser Asn Cys Arg Glu
Glu Pro Gly Thr Gly Leu Tyr Pro Asp Cys Cys Asn
Lys Val Val Cys Gly Glu Glu Glu Met Val Val Tyr
Pro Tyr Glu Glu Arg Ser Leu Arg Arg Tyr Tyr Phe
Ser Lys Phe

The invention claimed is:

1. A method for activating the motility of mammalian sperm, comprising:
   (a) contacting a sperm sample from a mammal with a quantity of La-1-like peptide agent comprising SEQ ID NO:1; and
   (b) optionally removing the La-1-like peptide agent.

2. The method according to claim 1, used for the treatment of male infertility.

3. The method according to claim 1, wherein the mammalian sperm is human, bovine, porcine, ovine, equine, goat, or of domestic animals.

4. The method according to claim 1, wherein the sperm to be activated has been previously frozen, or has been freshly ejaculated, or recovered from the epididymis, or from the testicle.

5. The method according to claim 1, wherein the La-1-like peptide agent is brought into contact in vitro, with sperm to be used in an artificial insemination procedure or in an in vitro fertilization procedure.

6. The method of claim 1, wherein the La-1-like peptide agent is brought into contact in vivo, with sperm to be used in a natural insemination procedure.

7. The method of claim 1 in which the mammalian sperm is in the form of a pharmaceutical composition for vaginal tract and/or cervical administration to a female before insemination, or in the form of a pharmaceutical composition for local administration to a male.

8. The method according to claim 1, wherein the sperm to be treated have an initial motility of between 1 and 30 μm/s.

9. The method according to claim 1, wherein the sperm to be treated have an initial motility of at least 30 μm/s.

10. The method of claim 1, further comprising the steps for selection of sperm for use in a human in vitro fertilization procedure, wherein the steps are:
   (c) observing and measuring sperm mobility using at least one parameter chosen from track speed, path velocity, natural amplitude, non-progressive velocity and progressive velocity; and
   (d) selecting the most motile sperm according to the criteria used in the particular IVF procedure to be used.

11. The method of selection of claim 10, wherein the procedure is a human in vitro fertilization procedure.

12. The method according to claim 1, wherein the method is used for increasing the fertility of an animal, and comprises steps (c) and (d):
   (c) artificially inseminating the female animal with said sperm sample and motility activating agent;
   (d) measuring the fertility rate.

13. The method of claim 11, wherein the human in vitro fertilization procedure is intra-cytoplasmic sperm injection (ICSI).

14. The method of claim 5, wherein the human in vitro fertilization procedure is intra-cytoplasmic sperm injection (ICSI).

15. The method of claim 7, wherein the local administration of the pharmaceutical composition to a male is by injection into the epididymis or testicle.

16. The method of claim 3, wherein the domestic animals are cats and dogs.

\* \* \* \* \*